(12) United States Patent
Hutchinson

(10) Patent No.: US 7,296,570 B2
(45) Date of Patent: Nov. 20, 2007

(54) THERMAL RETENTION PATIENT HOOD

(76) Inventor: Chad H. Hutchinson, 6775 Laurelhurst Dr. NW., Bremerton, WA (US) 98311

( * ) Notice: Subject to any disclaimer, the term of this patent is extended or adjusted under 35 U.S.C. 154(b) by 0 days.

(21) Appl. No.: 10/512,170

(22) PCT Filed: Jul. 10, 2003

(86) PCT No.: PCT/US03/21562

§ 371 (c)(1),
(2), (4) Date: Jan. 18, 2006

(87) PCT Pub. No.: WO2005/014111

PCT Pub. Date: Feb. 17, 2005

(65) Prior Publication Data

US 2006/0107950 A1    May 25, 2006

(51) Int. Cl.
*A62B 17/04* (2006.01)
(52) U.S. Cl. ................... 128/201.26; 128/857
(58) Field of Classification Search ........... 128/201.22, 128/201.23, 201.24, 201.25, 201.26, 201.29, 128/202.11, 202.18, 202.19, 206.29, 853, 128/854, 857; 2/410, 424, 423, 427, 428, 2/443, 171, 171.2, 172, 171.5, 173
See application file for complete search history.

(56) References Cited

U.S. PATENT DOCUMENTS

| | | | |
|---|---|---|---|
| 2,366,904 A | 1/1945 | Haugh | 128/143 |
| 3,789,839 A * | 2/1974 | Lund et al. | 128/201.25 |
| 4,019,508 A | 4/1977 | Der Estephanian et al. | 128/142.7 |
| 4,620,538 A | 11/1986 | Koegel et al. | 128/201.23 |
| 4,949,714 A | 8/1990 | Orr | 128/200.24 |
| 5,133,344 A * | 7/1992 | Jurrius et al. | 128/201.23 |
| 5,370,110 A * | 12/1994 | Corn | 128/201.22 |
| 5,492,116 A | 2/1996 | Scarberry et al. | 128/206.24 |
| 5,495,847 A | 3/1996 | Hu | 128/202.26 |
| 5,548,846 A * | 8/1996 | Bianchetti | 2/209.12 |
| 5,690,095 A * | 11/1997 | Glynn et al. | 128/201.23 |
| 5,918,314 A * | 7/1999 | Moses | 2/79 |
| 6,658,665 B2 * | 12/2003 | Dodge | 2/87 |
| 6,895,960 B2 * | 5/2005 | Fabin | 128/201.23 |
| 6,929,611 B2 * | 8/2005 | Koch | 600/549 |
| 2003/0111075 A1 | 6/2003 | Wen | 128/201.22 |

FOREIGN PATENT DOCUMENTS

GB    2 189 152 A    10/1987

* cited by examiner

*Primary Examiner*—Steven O. Douglas
(74) *Attorney, Agent, or Firm*—Seed IP Law Group PLLC

(57) ABSTRACT

A thermal retention hood for reducing heat loss from a patient's head during and following surgery includes an enclosure configured to cover the face and head of the patient, and configured to retain heat within the enclosure. The enclosure is at least partially transparent, to give a practitioner visual access to a patient's face. The hood further includes a scored line in the enclosure in a position corresponding to the patient's nose and mouth, a second scored line surrounding a region of the enclosure corresponding to the location of the patient's face, and a strap configured to secure an open end of the enclosure around the patient's neck. The hood may also include an absorbent pad within the enclosure, positioned to cover a portion of the back of the patient's head to absorb excess moisture.

17 Claims, 4 Drawing Sheets

THERMAL RETENTION PATIENT HOOD

BACKGROUND OF THE INVENTION

1. Field of the Invention

The invention relates to a surgical hood, and more particularly to a patient hood for retaining heat during surgery and recovery and to provide access for visual inspection and treatment.

2. Description of the Related Art

Recent clinical studies have demonstrated that mild perioperative and postoperative hypothermia is associated with several significant adverse effects on patient health. For example, in cases in which the core body temperature of a patient is moderately depressed, surgical wounds have been shown to heal more slowly, and be more susceptible to infection; duration of hospitalization may be two to three days longer, on average; blood loss during surgery is increased; incidences of serious cardiac complications are significantly more common; postanesthetic recovery is longer; and patient comfort during recovery is significantly reduced.

Maintaining a patient's core temperature during surgery can be a significant problem, inasmuch as the patient's metabolism is typically depressed due to anesthesia, and surgical theaters are commonly maintained at a relatively cool temperature, for the comfort of the surgical team. Meanwhile, the patient is commonly lightly draped, with portions of the patient's body exposed to the cool environment. Additionally, in cases where the patient is undergoing major surgery, the patient may lose significant body heat directly from the surgical site. Studies have also shown that the face and upper chest are far more sensitive to temperature loss than other regions of the body.

Body heat is lost by a combination of four sources:

(a) Conduction heat loss is the passage of heat energy from one mass to a cooler mass in direct contact therewith. In the case of a human body it occurs when a portion of the body is in contact with a surface or medium that is colder than that portion of the body. Heat is conducted from the warmer region to the colder region, thus drawing heat away from the body. In a cool environment, air in contact with the body will draw heat from the body.

(b) The second source of thermal energy loss is convection. Convection occurs in a fluid when one portion of the fluid is warmer than another, causing motion in the fluid, as the warmer, less dense, fluid rises, while the colder, denser fluid drops. Convection occurs in conjunction with conduction, when fluid, such as air, is warmed in a localized area by conduction through contact with a warmer mass, and is then carried away from the heat source by convection, which draws cool air into contact with the mass. Convection is also used to describe heat transfer due to motion or circulation of fluid by other sources. Thus, convection heat losses in a body increase when portions of the body are exposed to moving or circulating air that is cooler than the body.

(c) A third source of heat loss is evaporative heat loss. Evaporative heat loss occurs when a fluid in contact with a surface evaporates into the surrounding atmosphere. The energy required for the fluid to transition from a liquid state to a gaseous state is significant, and it is generally drawn from the surface in the form of heat. The human body's normal heat regulatory system exploits this phenomenon by producing sweat. As sweat evaporates from the skin, the skin is cooled, Thus, by conduction the body core temperature is regulated. During the course of a surgical procedure, cleansers, disinfectants, and other fluids are placed in contact with the body, together with the sweat that is normally produced. Heat is thus drawn from the body due to conduction and evaporation.

(d) The fourth source of heat loss is radiation. Radiation, mostly in the infrared spectrum, propagates outward from a warm mass and is a function of the absolute temperature of the mass, regardless of the ambient temperature, and, unlike the other three sources, is independent of any transmission medium. Radiation heat loss occurs when the energy radiated from a body exceeds heat either produced by the body or taken in by the body from other sources, such as conduction and convection.

Of the four sources of heat loss, conduction and convection contribute the most to the loss of core body temperature during surgery. An extensive examination of the causes and effects of heat loss to patients may be found in an article entitled *Complications and Treatment of Mild Hypothermia* (*Anesthesiology*, V95, No. 2, August 2001).

Methods and devices for mitigating the loss of heat during and immediately following surgery include the use of thermal blankets of various designs, which are placed around the patient during or following surgery. Also known is the use of heated surfaces on which a patient is placed during surgery. In U.S. Pat. No. 5,877,279, issued to Elting et al. on Mar. 30, 1999, a surgical garment is disclosed in which a patient is draped with a lightweight garment having several components that covers most of the body. The garment includes a hood that is configured to cover the top and the back of the patient's head, while leaving the patient's face exposed. However, this solution is incomplete, inasmuch as a significant percentage of heat loss occurs at the patient's face. This has been recognized, and occasional informal attempts have been made to address this issue. For example, in some cases practitioners have improvised by placing a plastic trash bag over a patient's head and face during surgery to prevent this heat loss.

There are, however, several drawbacks with using plastic bags. The bag obscures the patient's face, which should be visible to the anesthesiologist for the purpose of monitoring the patient's condition. The bag tends to be generally unwieldy and difficult to situate and typically the patient will have an endotrachial tube in the nose or throat, requiring an opening in the bag to permit passage of the tube. It is at least uncomfortable, and possibly dangerous for a patient to wear such a bag while conscious, such as during procedures requiring only local anesthesia or during recovery.

These and other disadvantages, including the difficulty of appropriately configuring such a bag, and the danger to the patient imposed by the obscuring of the patient's face, make the use of a plastic bag less than ideal.

BRIEF SUMMARY OF THE INVENTION

The disclosed embodiments of the invention provide a thermal retention hood for reducing all forms of heat loss from a patient's head during and following surgery. The hood includes a translucent or transparent plastic enclosure configured to cover the face and head of the patient in order to retain heat within the enclosure and limit heat loss due to the various sources described in the background section, above. The hood further includes a scored line in the enclosure in a position corresponding to the patient's nose and mouth, a second scored line surrounding a region of the enclosure corresponding to the location of the patient's face, and a strap configured to secure an open end of the enclosure around the patient's neck. The hood may also include an absorbent pad within the enclosure, with the pad positioned to cover a portion of the back of the patient's head to absorb excess moisture and retain heat.

According to another embodiment of the invention, a method of retaining body heat during surgery is provided, the method including the steps of trapping a layer of still air against the head and face of the patient by covering the patient's head and face with a plastic hood, inserting a tube into patient's nose or mouth via an opening provided in the hood, and tensioning a strap attached to the hood under the patient's chin to close the hood.

BRIEF DESCRIPTION OF THE SEVERAL VIEWS OF THE DRAWING(S)

DETAILED DESCRIPTION OF THE INVENTION

A thermal retention patient hood is disclosed and described with reference to FIGS. 1-3B.

Figure 1:
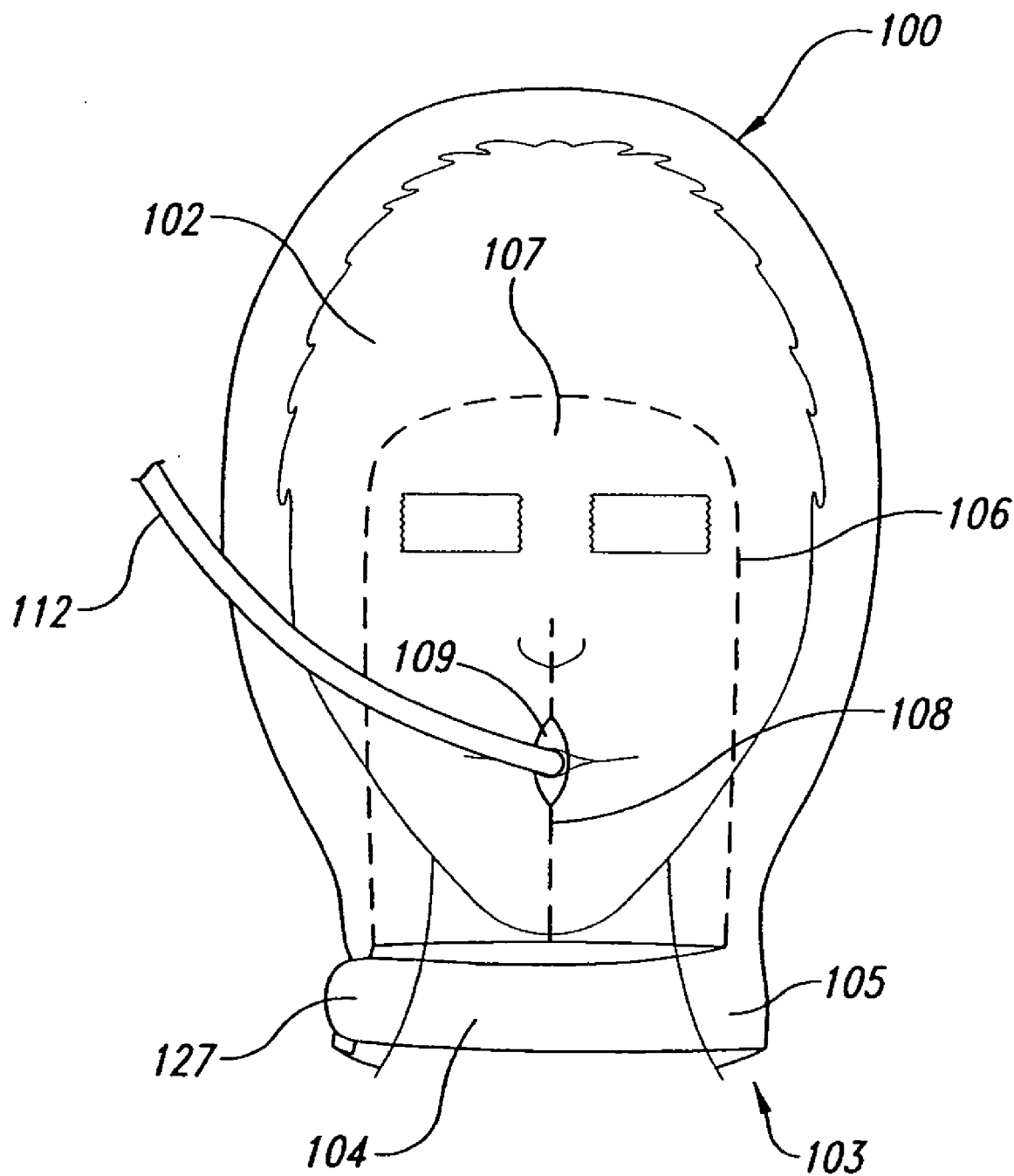
FIG. 1 shows a front view of a thermal retention hood in place on a patient's head according to one embodiment of the invention.

In FIG. 1 a patient 102 is shown from the front wearing a thermal retention hood 100 according to the principles of the invention. The hood 100 is formed from a suitable transparent plastic material such as polyethylene having a thickness of around 2 mils and is configured to be drawn over, and conform to, the shape of a normal sized adult human head, via an opening 103 at a bottom portion 105 of the hood 100. Although not shown, it will be understood that the thermal retention hood 100 may incorporate the use of gussets, tucks, darts, or other known methods of tailoring the hood to conform to the shape of a human head, and such methods will not be discussed in detail here.

The thermal retention hood includes a perforated line 108. A portion of the line 108 may be separated by gently pulling on either side of the line to create a hole 109 to provide access to the patient's mouth or nose. FIG. 1 shows an endotrachial tube 112 passing through the hole 109 and into the patient's mouth. Preferably the line 108 is vertical, but in some embodiments it may be desirable to use a horizontal line.

A second perforated line 106 defines a face panel 107 that is sized and shaped to cover the patient's face. By tearing along this line, the face panel 107 may be removed from the hood, thereby uncovering a portion of the patient's face while maintaining coverage over the majority of the face and head. In this way, the areas of the patient's face to which access is needed will be uncovered during recovery or during the performance of surgical procedures that require only local anesthesia. This gives the patient some freedom while maintaining coverage and heat retention over most of the patient's head.

Ideally, perforations are used to provide separability of the material of the hood 100. However, other weakening structures, such as scores or creases may be employed to permit controlled separation of the material. As used herein, the word score is used inclusively for such structures.

Figure 2:
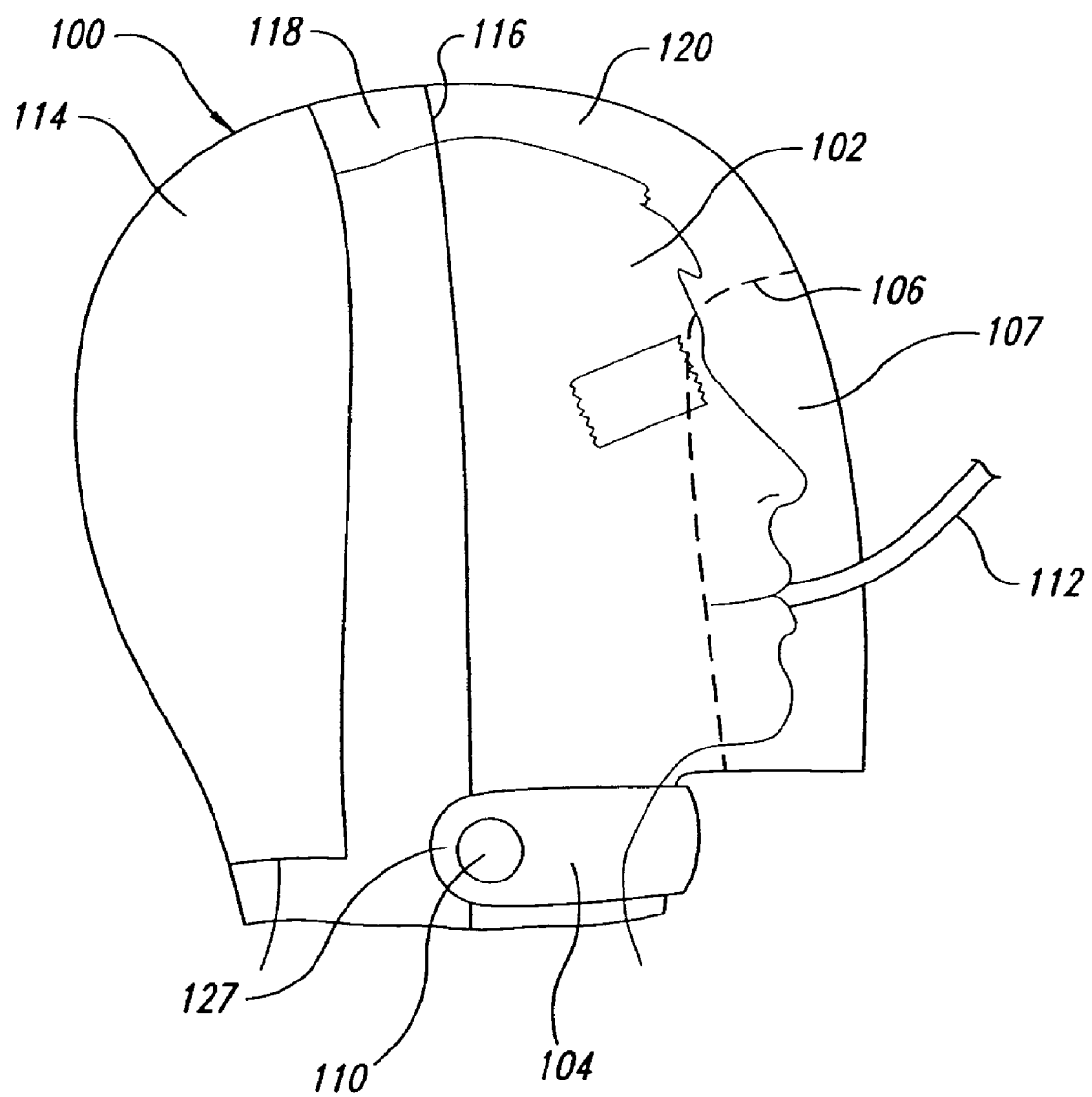
FIG. 2 shows a profile view of the embodiment of FIG. 1.

A strap 104 is attached to one side of the hood 100, and is configured to be drawn under the patient's chin and attached to the opposite side of the hood 100, thereby securely attaching the hood 100 to the patient's head. FIG. 2 shows a patch of adhesive 110 that may be provided on the strap 104. Alternatively, the strap 104 may be affixed under the patient's chin using hook and loop fasteners (Velcro™) or surgical tape, which is commonly available.

FIG. 2, which is a profile view of the embodiment of FIG. 1, shows a panel of absorbent material 114 affixed to or comprising the back of the hood 100. In one embodiment, the panel 114 is formed from material configured to absorb moisture and hold moisture in a central layer and remain relatively dry on a top layer, thus preventing fluid from passing through to the back side. In this application, the top layer is the side in contact with the back of the patient's head 102, while the backside is on the outside of the hood 100. One such material is commonly known in the industry as chux. The absorbent panel 114 functions to absorb moisture resulting from sweat and condensation within the hood 100, allowing the patient 102 to remain relatively dry.

According to one embodiment of the invention, the back section 118 of the hood 100 includes a heat reflective surface, such as Mylar™ to reduce radiant heat loss.

The front and back sections 120, 118 of the hood 100 can be formed from different kinds of material or fabric. It is desirable, however, that the front section 120, or at least the portion of the hood defined by the face panel 107 in the embodiment of FIGS. 1 and 2, be transparent or translucent to permit proper monitoring by a practitioner.

FIG. 2 also shows a welded line 116 passing from one side of the hood 100 to the other, marking the location where front and back sections 120, 118 of the hood 100 are welded together. As has been previously explained, the actual shape of the sections and configuration of weld lines are selected to permit the hood 100 to conform to the shape of a human head 102.

Figure 3A:
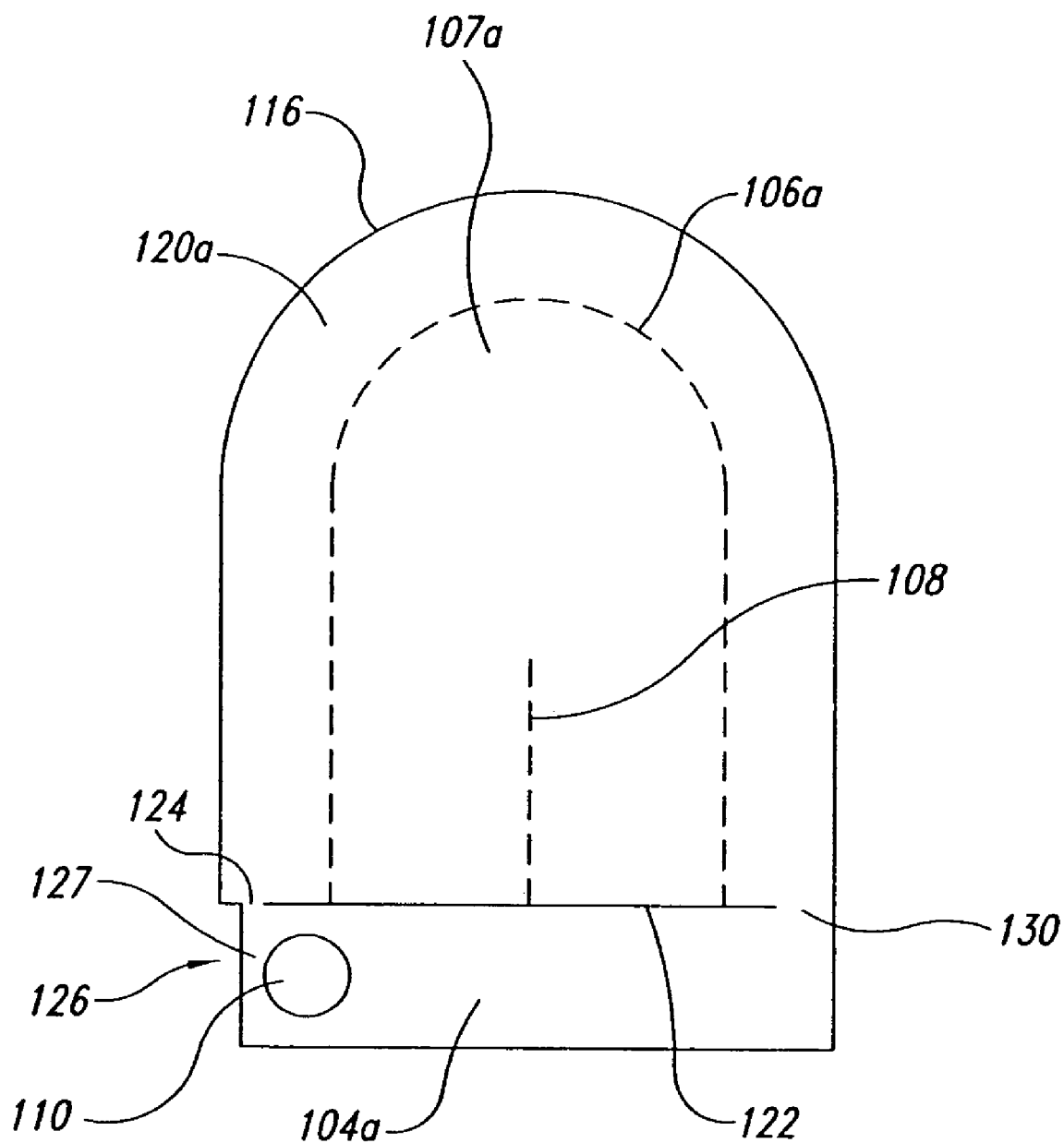
FIG. 3A shows a front view of a section of the hood according to another embodiment of the invention.

FIG. 3A shows a front section 120a of the thermal retention hood 100 according to one embodiment of the invention in which the strap 104a is shown as being defined from the rest of the front section 120a by a cut line 122, encompassing most of the width of the front section 120a of the hood 100. A region 130 on one side of the front section 120a remains uncut by the line 122 and defines a portion of the hood 100 where the strap 104a remains attached to the hood 100. A small tab 124 on the opposite end 127 of the strap 104 is provided to hold the strap 104a in position during the manufacturing process and during storage. A pressure sensitive adhesive patch 110 is provided on the inside of the strap 104a of the hood 100 and covered by a liner (not shown). In use, when the hood is to be attached to a patient the tab 124 is easily broken, permitting the end 127 of the strap 104a to be pulled away from the rest of the hood. The practitioner peels the liner from the pressure sensitive patch and draws the strap 104a more tightly under the chin of the patient. The pressure sensitive adhesive patch 110 is then pressed to a portion of the hood 100 on the opposite side of the patient's neck.

A notch 126 is provided in the front section 120a of the hood 100 such that, when the front section 120a is joined with the back section 118 of the hood 100 along weld line 116, the extreme end 127 of the strap 104a is not welded to a corresponding portion of the back section 118 of the hood 100. Thus, the end 127 of the strap is free to be tightened.

The perforated lines 106a, 108 are shown intersecting the cut line 122. A small portion of the perforated line 108 may be separated to provide passage for an airway tube. Upon separation of the perforated line 106a and removal of the face panel 107, the face panel 107a can be removed from the airway tube by separating the remainder of the perforated line 108.

It will be observed that all the cuts and perforations of the front section 120a of the hood may be made in a single manufacturing step.

Figure 3B:
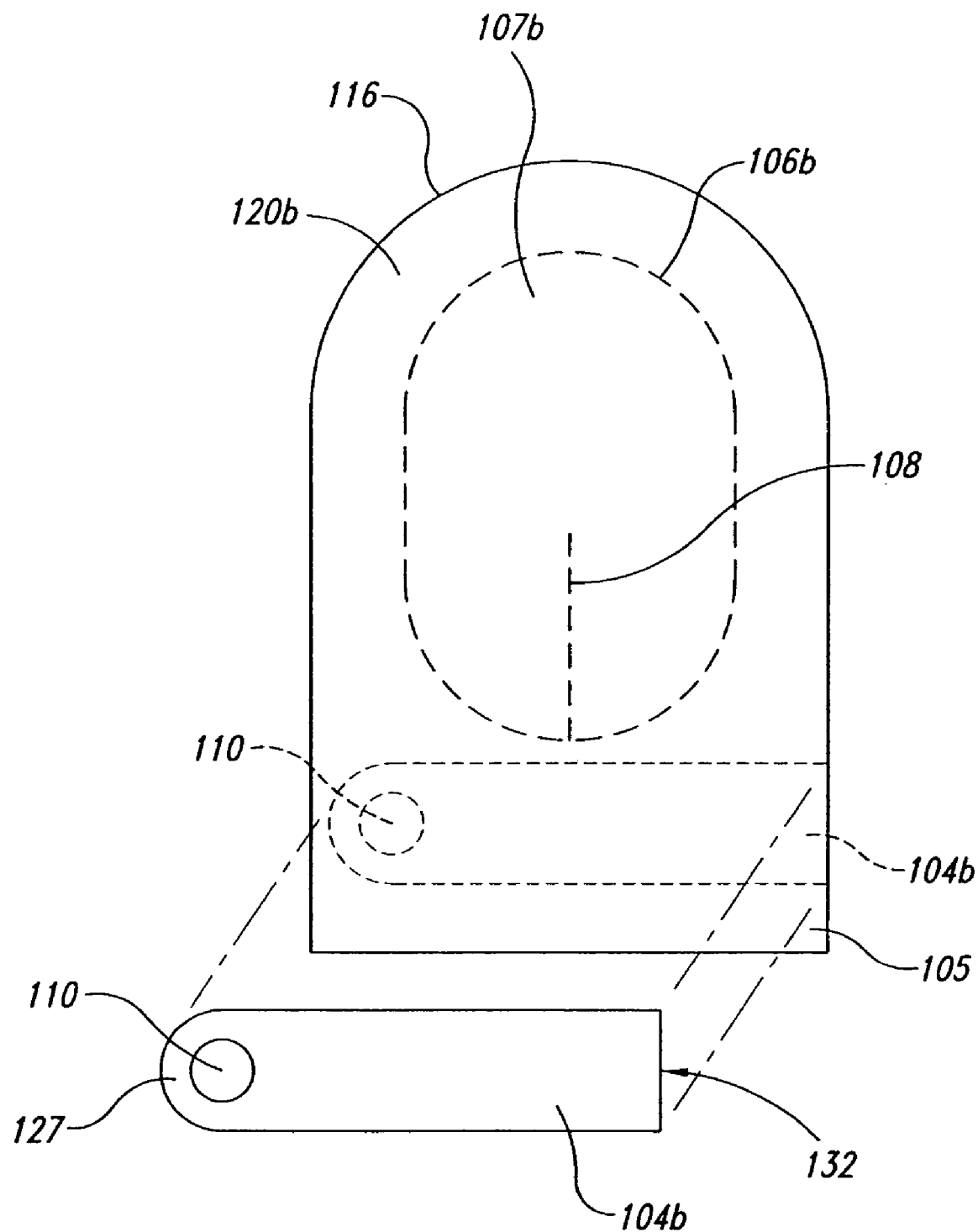
FIG. 3B shows a front view of a section of the hood according to an alternate embodiment of the invention.

FIG. 3B shows the front section 120b of the hood 100 according to an alternative embodiment. In the embodiment of FIG. 3B, the strap 104b is a separate piece of material. When the front section 120b is affixed to the back section 118 of the hood 100 at the weld line 116, the edge 132 of the strap 104b is welded to the hood in the position indicated by phantom lines in FIG. 3B. This is done at the same weld line 116 in the same manufacturing step that welds the front section 120b to the back section 118.

The perforated line 108 over the patient's mouth and nose is provided as described in previous embodiments. The perforated line 106b is in the form of an oval that corresponds to the position of the patient's face while wearing the hood 100. As previously described, this oval section 107b may be completely removed for the convenience of the surgeon or the patient. The adhesive patch 110b on the inside of the strap 104b is ideally formed of a relatively low tack adhesive. During manufacture, the adhesive patch 110b is applied to the strap 104b and employed to hold the strap flat against the front surface of the front section 120b. In use, the practitioner lifts the end 127 of the front strap 104b having the adhesive patch 110b, releasing the end 127 from the surface of the hood 100, and draws the strap further around the side of the patient's head or neck, while gathering the loose material of the hood 100 under the strap 104b beneath the patient's chin. The practitioner then presses the pressure sensitive adhesive patch 110 to a portion of the hood 100 on the opposite side of the patient's neck, as previously described with reference to other embodiments. The embodiment of FIG. 3B requires an additional manufacturing step to produce the strap, but provides a more complete coverage of the patient's face, inasmuch as the hood is sealed around the patient's neck by the strap 104b.

According to another embodiment of the invention, the hood 100 is provided with an elastic closure (not shown) around the bottom portion 105 of the hood. The elastic closure is attached around at least a portion of the circumference of the hood opening 103, sufficient to draw the opening close around the patient's neck, without tension enough to endanger the patient's airway or circulation. Naturally, in this embodiment, the strap 104 is not necessary to provide a secure attachment.

A key factor to effective heat retention is the trapping of an insulative layer of still air between the insulator and the skin, which the thermal retention patient hood does very effectively. Studies have shown that virtually any passive insulator reduces heat loss from skin surfaces by a significant amount, and that plastic is substantially as effective an insulator as other materials such as cotton, polypropylene fabric, or metalized plastic. Plastic, however, is superior to other materials in several respects. First, thermal retention hoods made from plastic of a type commonly used for the manufacture of bags, such as polyethylene in a range of around 1 to 4 mils thickness, is significantly less expensive than other materials. Additionally, thermal retention hoods made from lightweight plastic are very compact, and large numbers may be stored in a small space, as compared to the space required to store more expensive and bulkier fabric products. Thus, boxes of disposable thermal retention hoods may be purchased and stocked by surgical facilities at very low cost.

Polyethylene has been indicated for use in the manufacture of the hood 100. However, it will be recognized that any suitable material may be used to produce the hood, including other common formulations and thicknesses of plastics, fabrics, such as cotton, gor-tex™, polypropylene, and polyester, and non-woven material, such as Tyvek™.

While the thermal retention patient hood 100 has been described with reference to an adult sized hood, it will be recognized that the hood 100 may be configured to conform to heads of various sizes. For example, a hood 100 may be made to conform to the head of a very small infant, child, or of an adolescent or small adult. Accordingly, variations in the size or shape of a hood are considered to fall within the scope of the invention.

A temperature-sensing device may be affixed to an inner surface of the thermal retention hood 100 such that, when the hood is correctly positioned on a patient's head, the thermal retention device will be in contact with the patient's skin, usually the forehead, thereby providing the practitioner with a constant temperature reading.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A thermal retention hood for reducing heat loss from a patient's head during surgery and recovery, comprising:
    a flexible enclosure configured to enclose the face and head of the patient and retain heat within the enclosure;
    a first perforated line in the enclosure in a position corresponding to the patient's nose and mouth;
    a second perforated line defining a removable panel of the enclosure corresponding to the location of the patient's face, the removable panel adapted for removal to uncover only the patient's face while leaving the remainder of the enclosure on the patient's head to provide retention of heat within the remainder of the enclosure; and
    a strap configured to secure an open end of the enclosure around the patient's neck.

2. The hood of claim 1, further comprising adhesive on a free end of the strap.

3. The hood of claim 1, further comprising an absorbent pad within the enclosure and positioned to cover a portion of the back of the patient's head.

4. The hood of claim 1, further comprising a reflective surface within the enclosure and positioned to cover a portion of the back of the patient's head.

5. The hood of claim 1 wherein the enclosure is formed to have front and back sections.

6. The hood of claim 5 wherein the strap is formed by a cut line in the front section that substantially separates the strap from the front section.

7. The hood of claim 1 wherein the strap is formed separately from the enclosure and attached thereto.

8. The hood of claim 1, further comprising a temperature sensing strip affixed to an inside surface of the enclosure in a position corresponding to the patient's forehead.

9. A section of a hood configured to reduce heat loss by a patient's head during and following surgery, comprising:
    a first perforated line in a flexible material forming the section in a position corresponding to the nose and mouth of the patient; and a second perforated line in the material defining a removable panel of the enclosure corresponding to the location of the patient's face that is sized and shaped to be removed to uncover only the patient's face while leaving the remainder of the enclosure on the patient's head to provide retention of heat within the remainder of the enclosure.

10. The section of claim 9 further comprising a cut in the material defining a strap.

11. A method for reducing heat loss from a patient's head during and after surgery, comprising:

trapping a layer of still air against the head and face of the patient by covering the patient's head and face with a flexible hood;

inserting a tube into the patient's nose or mouth via an opening formed by tearing a first perforated line provided in the hood; and tensioning a strap attached to the hood under the patient's chin to close the hood.

12. The method of claim 11, further comprising peeling a liner from an adhesive patch positioned on a free end of the strap.

13. The method of claim 11, further comprising removing a section of the hood over the patient's face by tearing the hood along a second perforated line in the hood.

14. A hood for use with a surgical patient to reduce heat loss from the patient's head and facilitate observation of and unobstructed access to the patient's face, the hood comprising:

a flexible enclosure having a perforated line defining a removable front portion sized and shaped to cover the patient's face, and an attached cranial portion, the enclosure having an opening sized and shaped to be received over the patient's head, at least the front portion formed of at least translucent material to enable visual inspection of the patient's face, the enclosure further comprising an aperture formed by a linear perforation in the enclosure to provide access to the mouth and nose of the patient when the aperture is opened along the perforation, the removable front portion adapted to be manually removed from the enclosure while leaving the remainder of the enclosure on the patient's head.

15. The hood of claim 14 wherein a back portion of the enclosure is formed from an absorbent material chosen from among non-woven material, cotton, plastic, polyester, chux, and polypropylene.

16. The hood of claim 14, further comprising a strap attached to the enclosure near the opening and configured to close the opening around the patient's neck to minimize passage of air through the opening.

17. The hood of claim 14, further comprising an elastic member affixed to at least a portion of a circumference of the opening, configured to draw the opening closed around the patient's neck.

* * * * *